(12) United States Patent
Sauer et al.

(10) Patent No.: US 7,253,413 B2
(45) Date of Patent: Aug. 7, 2007

(54) GAS IDENTIFICATION SYSTEM

(75) Inventors: Terence Sauer, Westport, CT (US);
Gregg Ressler, Shelton, CT (US);
Robert Burch, Oconomowoc, WI (US);
William Desousa, Meriden, CT (US);
Maxim Frayer, Ridgefield, CT (US);
Kenneth Schreiber, Sandylook, CT (US)

(73) Assignee: Smiths Detection Inc., Danbury, CT (US)

( * ) Notice: Subject to any disclaimer, the term of this patent is extended or adjusted under 35 U.S.C. 154(b) by 70 days.

(21) Appl. No.: 10/986,760

(22) Filed: Nov. 15, 2004

(65) Prior Publication Data

US 2006/0102844 A1    May 18, 2006

(51) Int. Cl.
*G01J 5/02* (2006.01)
*G01J 3/28* (2006.01)
*G01N 21/01* (2006.01)
*G01N 23/10* (2006.01)
*G01N 23/12* (2006.01)

(52) U.S. Cl. .................. 250/339.13; 250/339.08; 250/343; 250/430; 250/576; 356/437; 356/440; 356/246; 356/326; 356/929

(58) Field of Classification Search .......... 250/339.13, 250/343, 429, 430, 576; 356/437, 440; 422/91
See application file for complete search history.

(56) References Cited

U.S. PATENT DOCUMENTS

| | | | |
|---|---|---|---|
| 4,170,901 A * | 10/1979 | Conkle et al. ......... 73/863.12 |
| 5,440,143 A | 8/1995 | Carangelo et al. |
| 5,508,525 A * | 4/1996 | Day et al. ............. 250/339.07 |
| 5,625,189 A * | 4/1997 | McCaul et al. ............ 250/343 |
| 5,691,487 A * | 11/1997 | Green et al. ............ 73/863.86 |
| 5,925,881 A * | 7/1999 | Wahlbrink ................. 250/343 |
| 6,083,298 A * | 7/2000 | Wang et al. .................. 95/99 |
| 2002/0024662 A1 | 2/2002 | Yuko et al. |

FOREIGN PATENT DOCUMENTS

FR         96/12952 A         5/1996

OTHER PUBLICATIONS

U.S. Environmental Protection Agency, Center for Environmental Research Information, Office of Research and Development. Compendium Method To-17: Determination of Volatile Organic Compounds in Ambient Air Using Active Sampling Onto Sorbent Tubes [online]. 2nd edition. Jan. 1997 [retrieved on Apr. 17, 2006]. (Cont'd in V below).*

(Continued)

*Primary Examiner*—David Porta
*Assistant Examiner*—Frederick F. Rosenberger
(74) *Attorney, Agent, or Firm*—Foley and Lardner LLP

(57) ABSTRACT

A system for identifying a gas sample includes a canister, a docking station, a thermal desorption device, and a spectrometer. The canister includes a sorbent and a valve. The docking station is configured to removably engage the canister. When the canister is engaged with the docking station, the canister is capable of fluid communication with a gas cell via the valve.

53 Claims, 11 Drawing Sheets

OTHER PUBLICATIONS (Cont'd from U above) Retrieved from the Internet: <URL:http://www.epa.gov/ttn/amtic/files/ambient/airtox/to-17.pdf>, Section 8.*

Pogodina, Olga A. et al., "Combination of Sorption Tube Sampling and Thermal Desorption with Hollow Waveguide FT-IR Spectroscopy for Atmospheric Trace Gas Analysis: Determination of Atmospheric Ethene at the Lower ppb Level", *Analytical Chemistry*, vol. 76, No. 2, Jan. 15, 2004, pp. 464-468.

Patent Abstracts of Japan, vol. 2000, No. 12 (Jan. 3, 2001) & JP 2000 241313 A(Nippon Telegr & Teleph Corp <NTT>) (Sep. 8, 2000).

* cited by examiner

GAS IDENTIFICATION SYSTEM

FIELD OF THE INVENTION

The present invention relates generally to the field of detection and identification of unknown gases and more particularly to infrared gas identification systems and methods.

BACKGROUND OF THE INVENTION

The ability to detect and identify unknown gases is increasingly important for homeland defense and other safety reasons. For example, the Occupational Safety and Health Administration (OSHA) requires that a four-gas meter be carried by all personnel working in a confined space. These meters are also carried by all hazardous material (HAZMAT) teams. While these meters can alert an operator to the presence of a gas, the meters cannot identify the components of the gas. It is advantageous to be able to differentiate and identify unknown substances to determine the type and extent of hazard present in an environment. Gas monitoring instruments are useful in a variety of situations. For example, a gas monitoring system can protect personnel from otherwise undetectable hazards that may exist in workplace environments. Gas monitoring systems can also protect and assist a first responder in situations where hazardous material cleanup may be necessary.

Various methods for identifying unknown chemicals are known. These methods include, for example, various forms of vibrational spectroscopy such as infrared spectroscopy, nuclear magnetic resonance spectroscopy, gas chromatography, mass spectrometry, ion mobility spectrometry, and x-ray crystallography. Each of these methods has its own benefits and drawbacks. Often the type of method used to identify an unknown sample will depend on the form of the sample and the information which needs to be identified.

Infrared (IR) spectroscopy is particularly useful for the identification of unknown gases. Spectroscopic analysis using radiant energy in the infrared region of the electromagnetic radiation spectrum is a primary technique for chemical analysis of molecular compounds. The infrared spectral region extends from 0.7 to 250 micrometers, wherein the mid-IR region is generally considered to cover the region from about 2.5 to about 25 micrometers, which is commonly used for molecular vibrational spectroscopy. The mid-IR region of the spectrum arises from the fundamental movement of chemical bonds in molecules. When a beam of infrared energy is passed through an unknown sample, a spectrum, or characteristic fingerprint, of the molecules making up the sample is obtained. The unique spectrum obtained allows the components of the sample to be identified using a fundamental understanding of vibrational spectroscopy by comparison with a library of known compounds.

Fourier Transform infrared (FTIR) spectroscopy is especially suitable for quick identification of unknown samples due to its high sensitivity and rapid operational speed. However, FTIR suffers significant limitations due to technical and size limitations inherent in the detectors used in FTIR instruments making the instruments difficult to use in a field setting. These limitations are more pronounced when a sample is gaseous because the concentration of unknown in the sample is typically lower in a gas than in a liquid or solid sample. Prior approaches to increasing detection sensitivity include treatment of the sample or sample collection procedure and modifications to an instrument's detector.

One approach to modification of the instrument's detection system includes the use of long path cells. Long path gas cells can be sensitive enough to not require pre-concentration of a sample, but such devices generally require liquid nitrogen cooled detectors which are practicable only in a laboratory setting. Additionally, the volume and mass of these cells is large, requiring a larger sample, which must be collected and transported to a laboratory for analysis.

Another approach to analyzing gas samples involves absorption of a sample onto a sorbent followed by thermal desorption of the sample into a hollow wave guide acting as a gas cell for FTIR. See, Pogodina et al, *Anal. Chem.* 76, 464-68 (2004). Because a waveguide transmits less energy than a standard long path gas cell, this method also requires a research grade FTIR outfitted with a liquid nitrogen cooled detector.

Despite the various methods and techniques used in developing gas detection and identification systems, current systems are often expensive and bulky, which severely limits their usefulness in the field. Furthermore, current systems and methods do not allow for sample collection followed by decontamination of the sample collection device either prior to or immediately after sample analysis and prior to removal from the site of potential contamination to thereby prevent contamination of other locations and personnel.

SUMMARY OF THE INVENTION

Accordingly, there is a need in the art for a durable, portable gas detection and identification system capable of collecting and analyzing unknown gas samples in the field.

According to an embodiment of the present invention, a system for identifying a gas sample is provided. The system includes a canister having a sorbent and a valve; a docking station for removably engaging the canister; a thermal desorption; and a spectrometer. The canister is capable of fluid communication with a gas cell via the valve when the canister is engaged with the docking station.

According to another embodiment, a method of identifying a gaseous sample is provided. The method includes providing a sorbent disposed in a tube; adsorbing an atmospheric gas to the sorbent; desorbing the atmospheric gas from the sorbent to yield a gaseous sample; circulating a carrier gas through the tube so that the carrier gas mixes with the gaseous sample; transferring the gaseous sample to a gas cell; activating a spectrometer in optical contact with the gas cell; obtaining a spectrum of the gaseous sample; and comparing the obtained spectrum of the gaseous sample with a set of known spectrum values.

According to another embodiment, a gas cell is provided. The gas cell includes a housing defining a substantially closed compartment; a spherical optic in an objective position; and a flat optic in a field position. The flat optic is configured to permit a beam to enter and exit the compartment. The spherical optic is configured to produce two reflections of the beam in the compartment and the flat optic is configured to produce one reflection of the beam in the compartment so that the beam passes through the compartment four times.

According to another embodiment, a portable device for analyzing a gaseous sample is provided. The portable device includes a canister having a sorbent for adsorbing the gaseous sample; a gas cell in optical communication with a spectrometer; a docking station configured for removable engagement with the canister; and a computer system for analyzing data from the spectrometer. The canister is adapted for fluid communication with the gas cell when the canister is engaged with the docking station.

Other features, objects, and advantages of the present invention are apparent in the detailed description that follows. It should be understood, however, that the detailed description, while indicating embodiments of the invention, is given by way of illustration only, not limitation. Various changes and modifications within the spirit and scope of the invention will become apparent to those skilled in the art from the detailed description.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

DETAILED DESCRIPTION

Figure 1:
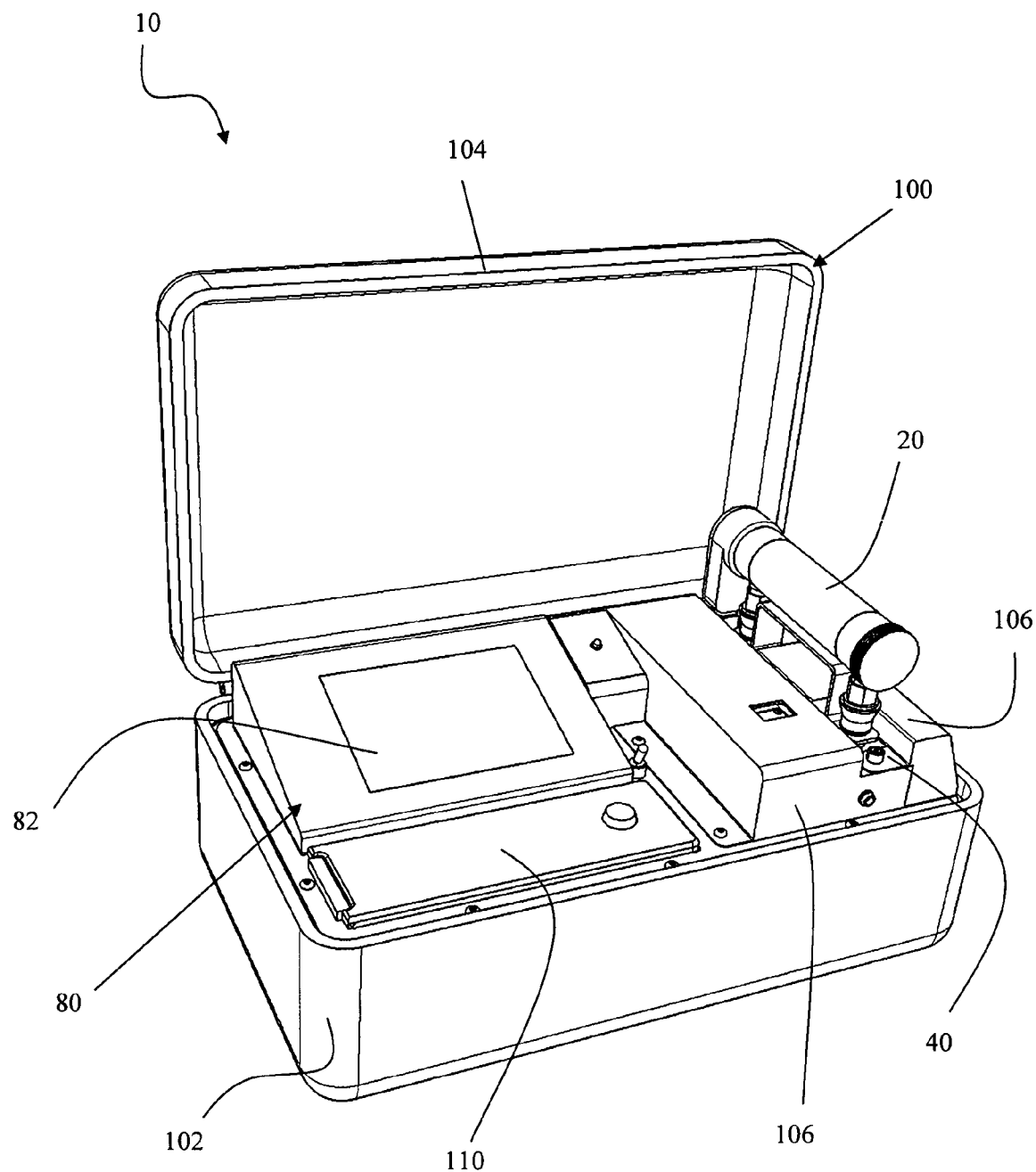
FIG. 1 is a front perspective view of an embodiment of a device for identifying a gas sample according to the present invention.

The present invention relates to an apparatus and method for the identification of unknown chemicals in a gaseous sample. In particular, the present invention provides a gas detection and identification system for collection and analysis of a gas sample. The system is configured to be durable and suitably sized for portability and transport to on-site and field locations. As a result, a user can utilize the system in non-laboratory environments, such as on-site at hazardous material spills and/or in the battlefield to detect chemical warfare agents. In this manner, technology for identifying potential chemical hazards is made readily available to HAZMAT teams, facility security professionals, military forces, and first responders at locations on-site and in the field.

FIGS. 1-11 show an embodiment of a device 10 for collecting and identifying a gas sample. The device 10 includes a sampling canister 20, a thermal desorption device 30, a docking station 40, a transfer mechanism 50, a gas cell 60, and a spectrometer 70.

Figure 7:
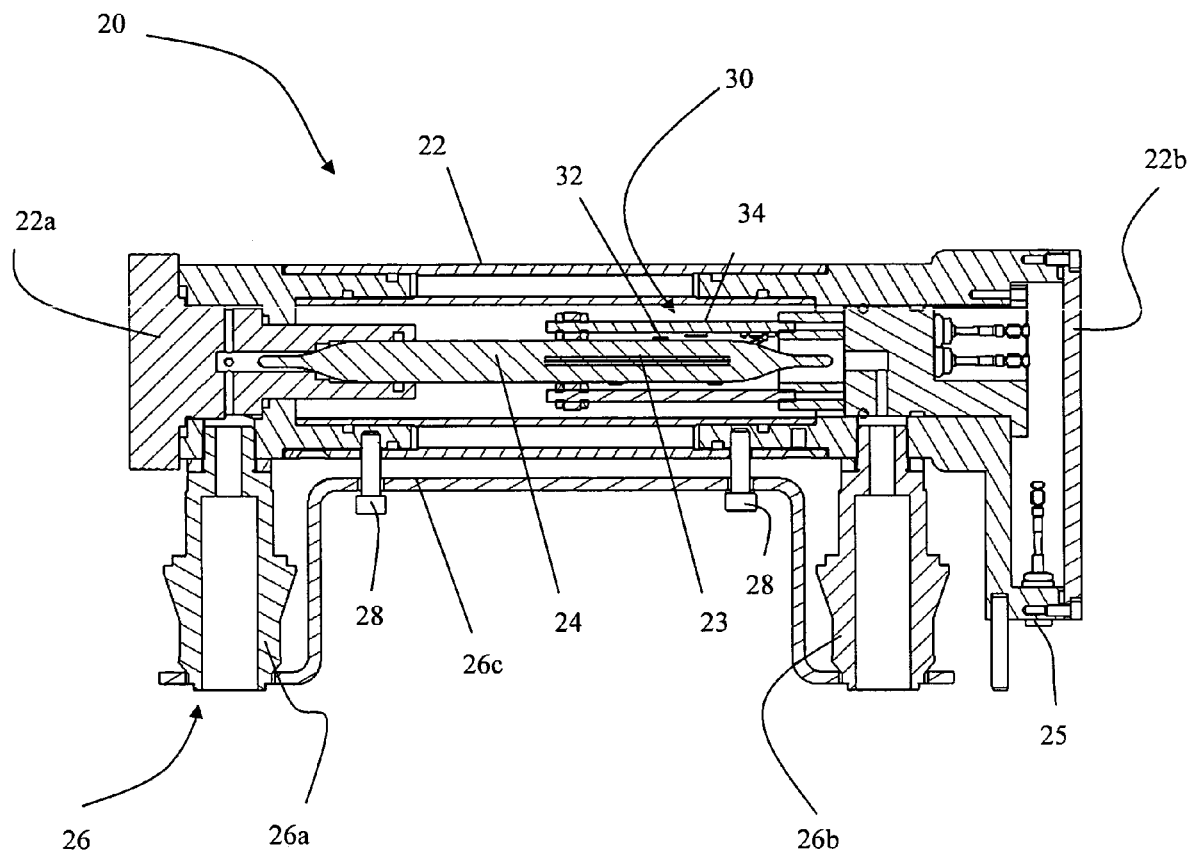
FIG. 7 is a cross sectional view of the sampling canister of FIG. 6 taken along the line VII-VII.
Figure 8:
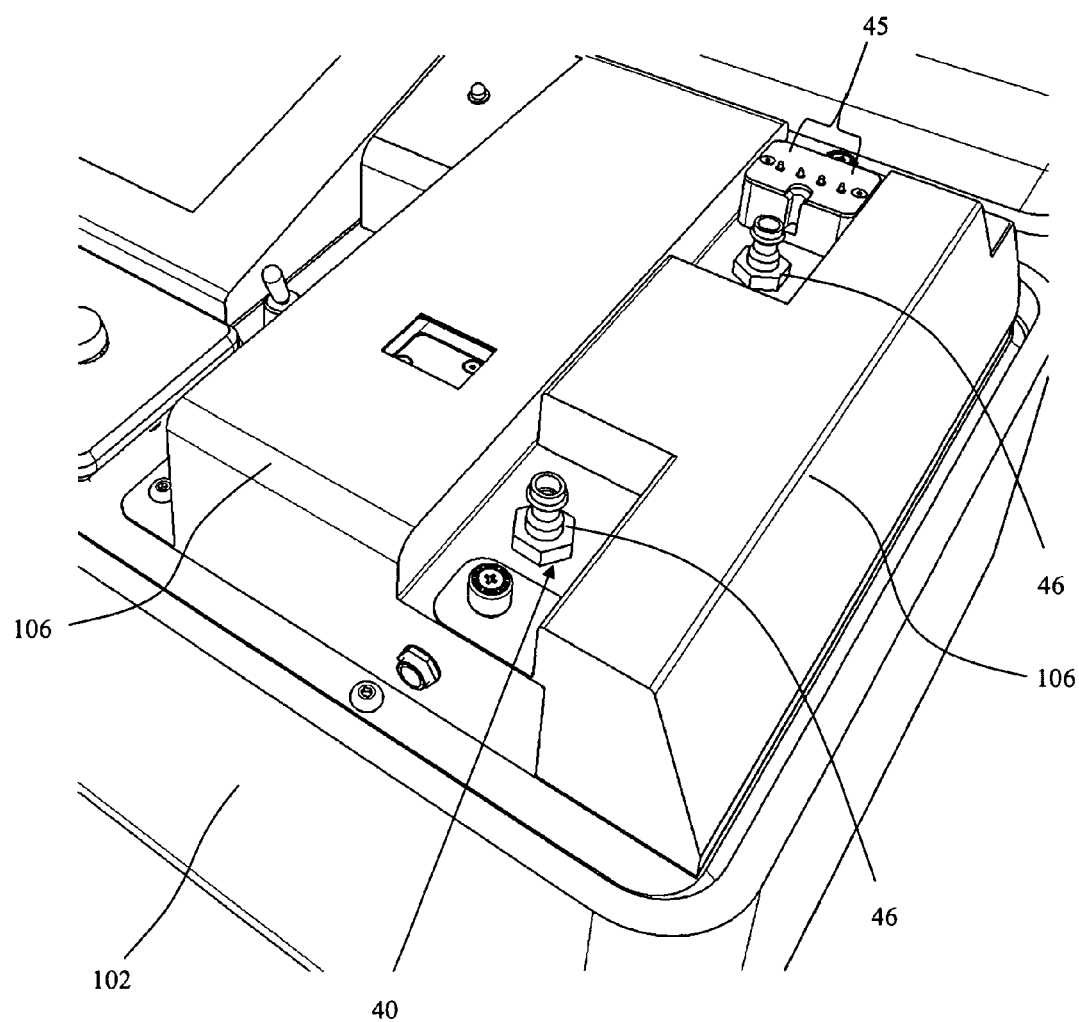
FIG. 8 is a perspective view of a docking station of the device of FIG. 1.

The sampling canister 20 is configured to enable the device 10 to collect a gaseous sample of a potentially contaminated environment and to determine whether the sample contains a hazardous agent. Sampling of the environment may be accomplished by drawing the gaseous sample from the environment through the sampling canister 20. For example, as shown in FIG. 7, the sampling canister 20 may include a housing 22, a sampling tube 24 disposed within the housing 22, and a valve mechanism 26 that seals an interior of the sampling tube 24 from the environment. To obtain a sample of the environment, a user connects the sampling canister 20 to a sampling pump 90 (shown in FIG. 5), actuates the valve mechanism 26, and draws the gaseous sample from the environment through the interior of the sampling tube 24.

The sampling tube 24 is configured to contain a sorbent 23 capable of absorbing or adsorbing the gaseous sample from the environment as the gaseous sample is drawn through the interior of the sampling tube 24. The sampling tube 24 may be a substantially airtight vessel constructed of any material that is capable of holding a gas sample and that is compatible with the sorbent 23. For example, the sampling tube 24 may be made of stainless steel or aluminum. In an exemplary embodiment, the sampling tube 24 is constructed of glass. The sampling tube 24 may be configured to be reusable (e.g., by replacing the sorbent 23). Alternatively, the sampling tube 24 may be a disposable, pre-packaged, sealed consumable configured to be used for collection of a single sample. After a sample is collected and analyzed, the disposable consumable may be removed from the sampling canister 20 and discarded.

The dimensions of the sampling tube 24 can be tailored to the parameters of the intended application and can vary depending upon, for example, the environment to be sampled and/or the amount of sorbent required to obtain a sample of sufficient size. A diameter of the sampling tube 24 may be, for example, approximately 6 mm to 10 mm, and a length of the sampling tube 24 may be approximately 70 mm to 250 mm. In an exemplary embodiment, the diameter of the sampling tube 24 is approximately 8 mm, and the length of the sampling tube is approximately 110 mm. The sampling tube 24 may contain, for example, approximately 50 mg to 1000 mg of the sorbent 23. According to one embodiment, the sampling tube 24 is sized to contain approximately 150 mg of the sorbent 23.

The sorbent 23 is configured to capture the gaseous sample as the gaseous sample is drawn through the sampling tube 24. For example, the sorbent 23 may consist of small beads of material contained in the sampling tube 24. The sorbent material may be any suitable material known in the art for adsorbing or absorbing a wide variety of compounds, including low to high boiling organics, such as methane, propane, n-pentane, acetone, isopropanol, toluene, m-xylene, 1,2-dichlorobenzene, n-dodecane, nicotine, 1-dodecanol, ethanol, methanol, and thiodiethanol, as well as inorganic components, such as HCN and ammonia. Other compounds/components include carbon monoxide, butane, methyl ethyl ketone, hydrogen sulfide, and agents used in weapons of mass destruction such as, for example, sarin, mustard gas, tabun, and VX. A suitable sorbent material is designated as that which produces an acceptable concentration factor for the sample components contemplated. The concentration factor is defined as (concentration of sample in a gas cell)/(concentration of sample in atmosphere being sampled). Examples of suitable sorbent materials include, charcoal, ANASORB®, ANASORB® GCB2 (graphitized carbon black with a low surface area (10 to 13 $m^2/g$)), ANASORB® GCB1 (graphitized carbon black with a moderate surface area (100 to 200 $m^2/g$)), ANASORB® CMS (carbon molecular sieve), carbon, such as carbon molecular sieve, CHROMOSORB® (diatomaceous earth-based supports), CHROMOSORB-102' (styrene/divinylbenzene synthetic porous polymer support), CHROMOSORB-104® (polar acrylonitrile-divinylbenzene), CHROMOSORB-106® (styrene/divinylbenzene, non-polar), CHROMOSORB-108® (moderately polar acrylic ester resin), FLORISIL® 226 (magnesium silicate), PORAPAK® (polymer beads, Waters Corp.), POROPAK-N® (polymer beads, Waters Corp.), PORAPAK-Q® (polymer beads, Waters Corp.), PORAPAK-R® (polymer beads, Waters Corp.), PORAPAK-T® (polymer beads, Waters Corp.), polyurethane foams (PUF), silica gel, TENAX® (polymer resin), TENAX® 226 (polymer resin), TENAX® GR (polymer resin based on 2-diphenylene oxide with graphite), TENAX® TA (polymer resin based on 2,6-diphenylene oxide), XAD® (polymeric adsorbent, Rohm and Haas Co.), XAD®-2 (polymeric adsorbent, Rohm and Haas Co.), XAD®-4 (polymeric adsorbent, Rohm and Haas Co.), XAD®-7 (polymeric adsorbent, Rohm and Haas Co.), and/or a combination of one or more sorbent materials. In one embodiment, the sorbent is TENAX® TA. In an exemplary embodiment, a combination of TENAX® and carbon may be used to trap both high and low molecular weight samples.

A suitable concentration factor is that which allows for a desirable identification limit (IL). In one embodiment, a desirable IL is one half the Immediately Dangerous to Life and Health (IDHL) value. In another embodiment, IL is defined as the concentration of a compound that produces a sufficiently high signal-to-noise spectrum to result in a spectral library match of that compound with a dot product correlation of 0.9 on a scale from 0 to 1. The IL can range from approximately 1 ppm to 1000 ppm, approximately 10 ppm to approximately 100 ppm, and from approximately 5 to approximately 15 ppm. In one embodiment, the IL is approximately 10 ppm.

Figure 4:
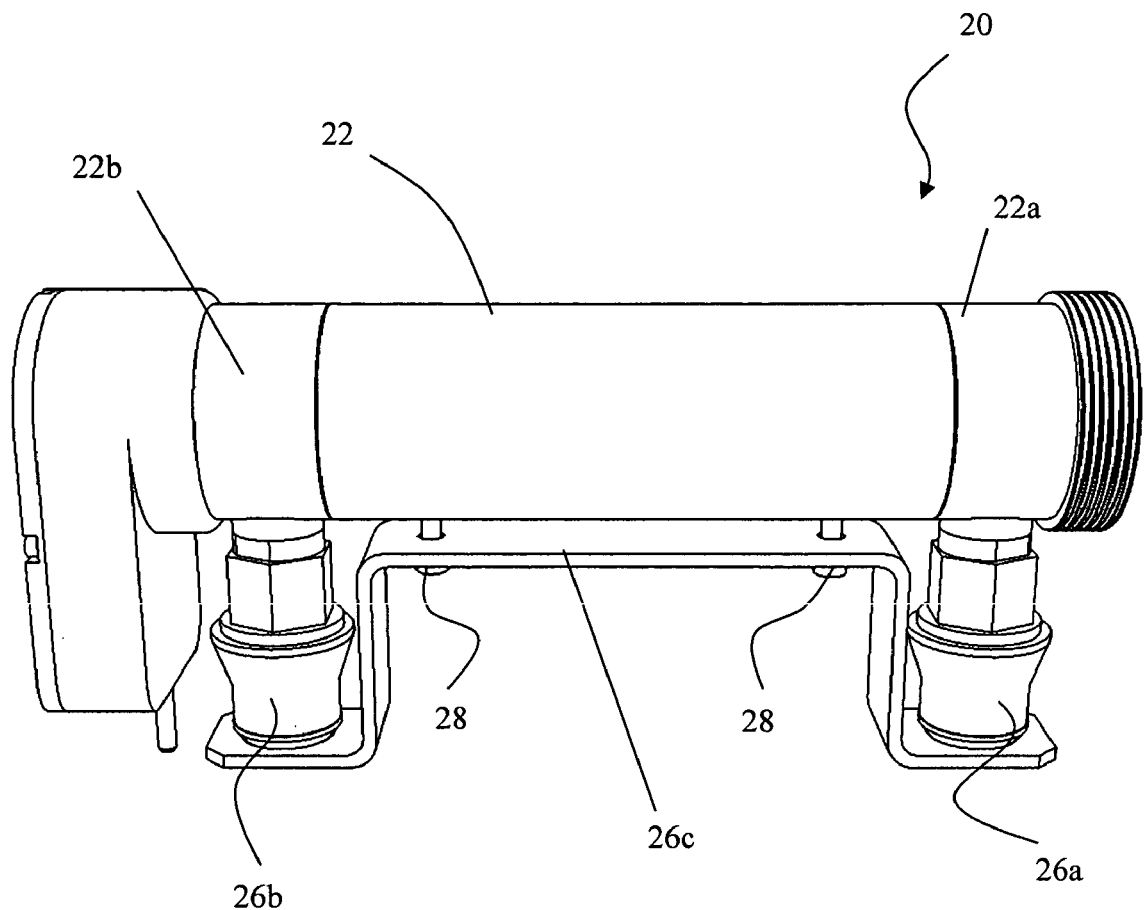
FIG. 4 is a left perspective view of a sampling canister of the device of FIG. 1.
Figure 5:
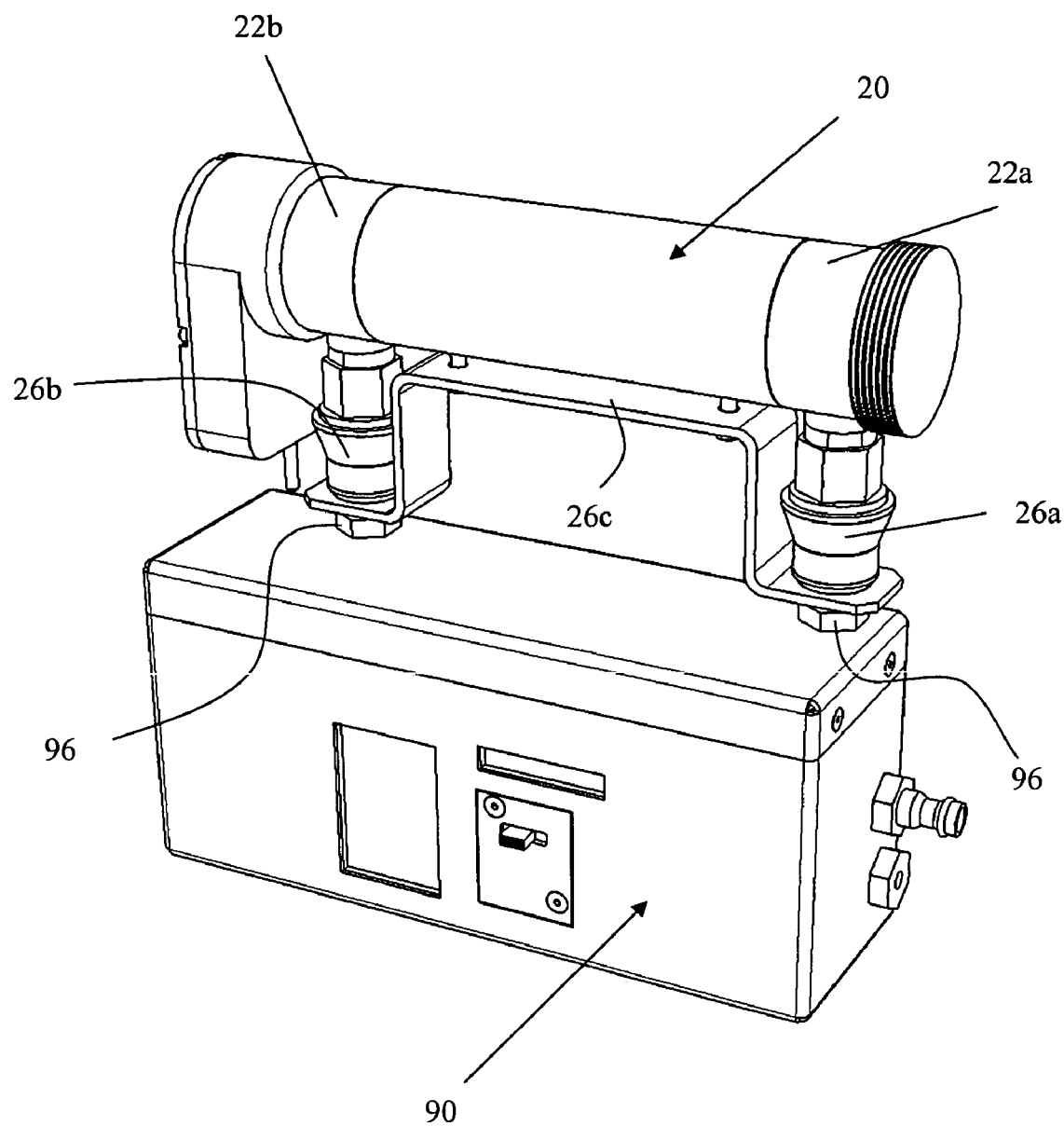
FIG. 5 is a left perspective view of the sampling canister of FIG. 4 in a sampling configuration.
Figure 6:
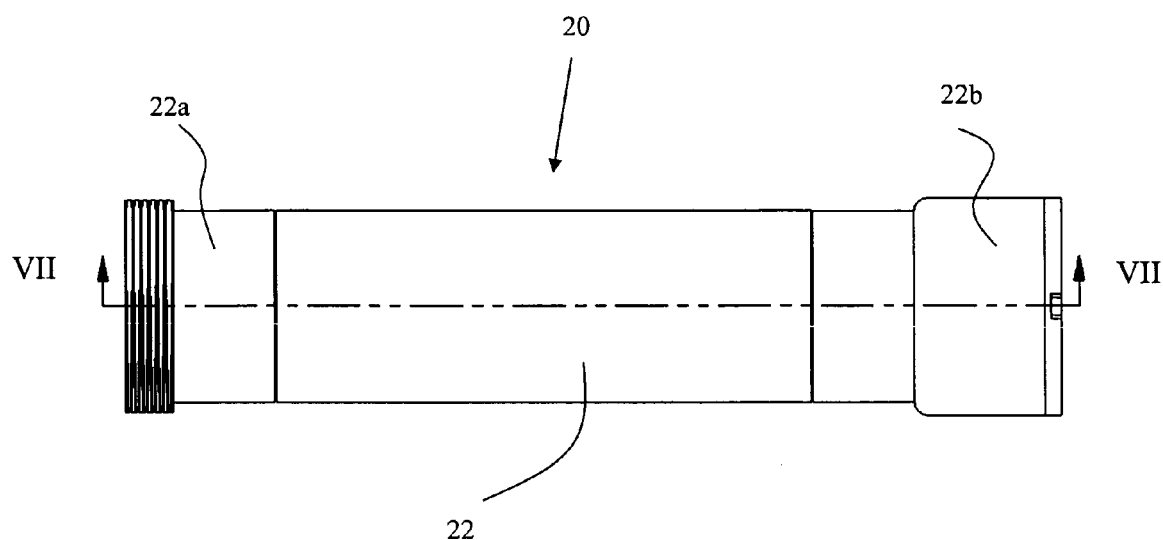
FIG. 6 is a top plan view of the sampling canister of FIG. 4.

The housing 22 of the sampling canister 20 is configured to accommodate the sampling tube 24 so that the sampling tube 24 is isolated from the environment and is protected from damage. For example, as shown in FIGS. 4-6, the housing 22 may be a sealed container having a first end 22a and a second end 22b. The housing 22 may be constructed of any material that is sufficiently durable and rigid such as, for example, aluminum, plastic, a polymer, and/or a resin. In an exemplary embodiment, the housing 22 is constructed of stainless steel due to its strength and compatibility with samples and decontamination solutions.

Figure 3:
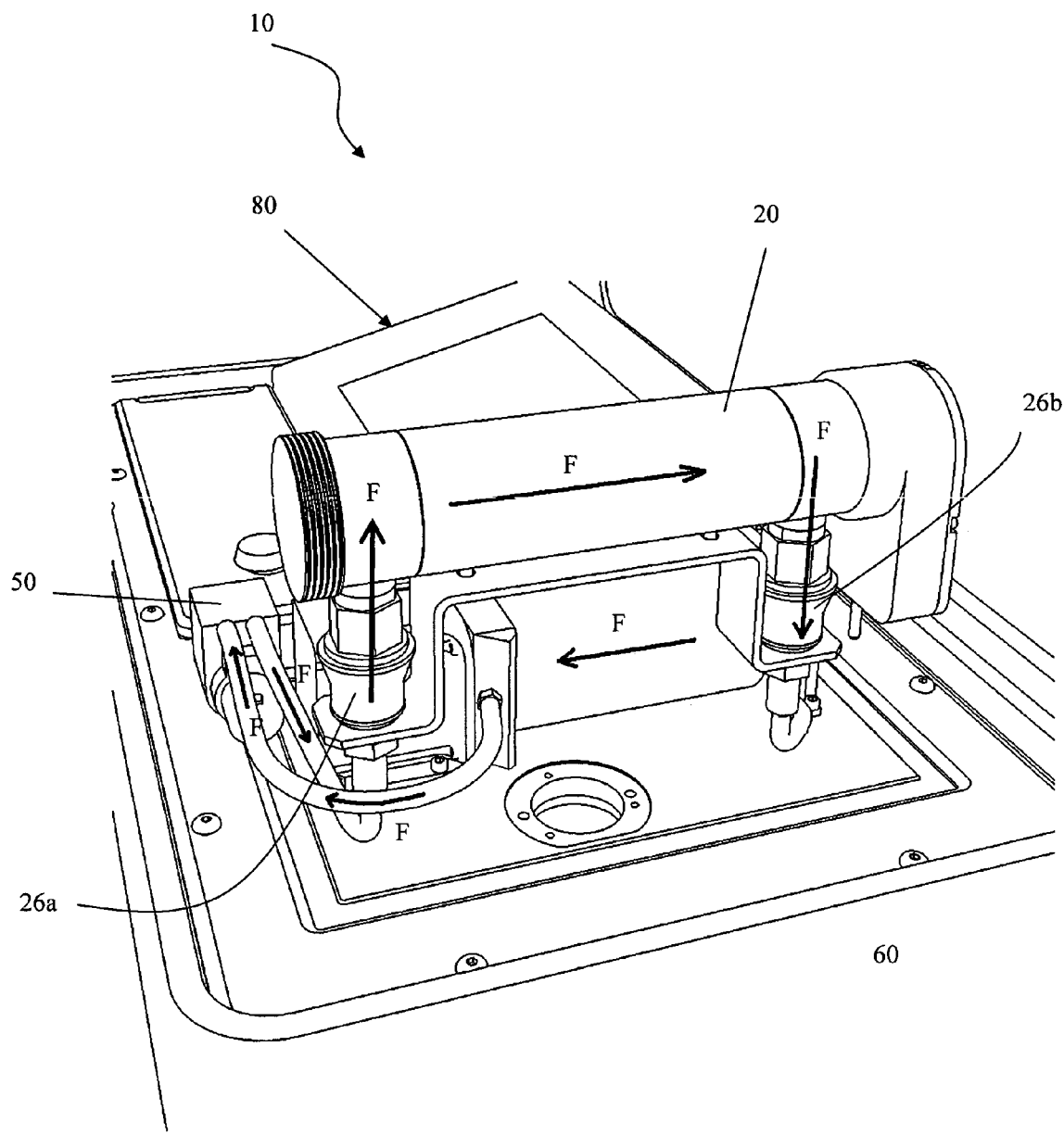
FIG. 3 is a right perspective view of the device of FIG. 1 showing a gas flow path.

The valve mechanism 26 of the sampling canister 20 is connected to the housing 22 and allows the interior of the sampling tube 24 to be exposed to an environment external to the sampling canister 20. The valve mechanism 26 thereby enables gas from the environment to be circulated through the sampling tube 24 to effect an exchange of gases between the interior of the sampling tube 24 and the environment. For example, the valve mechanism 26 may include a first valve 26a disposed at the first end 22a of the housing 22 and a second valve 26b disposed at the second end 22b of the housing 22. As shown in FIG. 3, the first valve 26a may be an inlet for a flow of gas F, and the second valve 26b may be an outlet for the flow of gas F.

The valves 26a and 26b can be actuated in any known manner between a closed position where the interior of the sampling tube 24 is sealed from the environment and an open position where the interior of the sampling tube 24 is exposed to the environment. In an exemplary embodiment, the valves 26a and 26b are adapted to automatically move from the closed position to the open position when the valves 26a and 26b are connected to the sampling pump 90 (shown in FIG. 5) and when the valves 26a and 26b are connected to the docking station 40 (shown in FIG. 2). For example, the valves 26a and 26b may be quick disconnect couplings that connect to corresponding couplings 46 (shown in FIG. 8) on the docking station 40 and to corresponding couplings 96 on the sampling pump 90. The quick disconnect couplings may be any known quick disconnect couplings such as, for example, couplings used for compressed air hoses or those manufactured by Colder Products Company (CPC). Additionally, suitable couplings should be compatible with samples and decontamination solutions. For example, couplings may be made of stainless steel. The valves 26a and 26b may be connected to the docking station 40 and to the sampling pump 90 by pressing the valves 26a and 26b onto the corresponding couplings 46 and 96, respectively. The valves 26a and 26b may be retained on the corresponding couplings 46 and 96, for example, by a detent mechanism (e.g., a ball and spring assembly) in the quick disconnect couplings.

The valve mechanism 26 may also include a control mechanism 26c to facilitate removal of the sampling canister 20 from the docking station 40 and from the sampling pump 90. As shown in FIG. 4, in one embodiment, the control mechanism 26c may be an elongated member that is attached to the housing 22 (e.g., by fasteners 28 such as bolts) and that is engaged with each of the valves 26a and 26b. The elongated member may be formed, for example, from metal such as stainless steel or aluminum. When the control mechanism 26c is moved in an upward direction (i.e., in a direction toward the canister 20), the control mechanism 26c exerts an upward force on the valves 26a and 26b, which actuates the detent mechanism in the quick disconnect couplings thereby releasing the valves 26a and 26b from the corresponding couplings 46 and 96 on the docking station 40 and the sampling pump 90, respectively. When the valves 26a and 26b are disconnected, the valves automatically return to the closed position to thereby seal the interior of the sampling tube 24 from the environment.

As shown in FIG. 5, when the valves 26a and 26b are connected to the sampling pump 90, the sampling canister 20 is in a sampling configuration. The sampling pump 90 may be, for example, an air pump such as a portable, battery operated air pump. In the sampling configuration, a gaseous sample of the environment may be collected. To collect the gaseous sample, the valves 26a and 26b are connected to the sampling pump 90 substantially as described above. The sampling pump 90 is turned on and draws a gaseous atmospheric sample from the environment through the sampling tube 24. As the gaseous sample is drawn through the sampling tube 24, the gaseous sample contacts the sorbent 23 in the sampling tube 24 and is at least partially adsorbed or absorbed by the sorbent 23. When sampling is complete, the sampling pump 90 is turned off. As described above, disconnecting the sampling canister 20 from the sampling pump automatically closes the valves 26a and 26b. Alternatively, the valves 26a and 26b may be configured for manual operation. When the valves are closed, the gaseous sample is retained in the sampling tube 24 of the sampling canister 20.

The gaseous sample may be collected by drawing the environmental sample through the sampling tube 24 at a rate in a range of approximately 10 mL/min to approximately 500 mL/min. In an exemplary embodiment, the sample is drawn at a rate in a range of approximately 50 mL/min to approximately 250 mL/min. In a further embodiment, the sample is drawn at a rate of approximately 200 mL/min. The sampling period is determined based on the sampling rate and the amount of sample to be collected. For example, the sampling period may be in a range of approximately 1 minute to approximately 60 minutes. In one embodiment, the gaseous sample is drawn through the sampling tube 24 for approximately 5 minutes to approximately 30 minutes. In a further embodiment, the sample is drawn through the sampling tube 24 for approximately 10 minutes. In an additional embodiment, the sample is drawn through the sampling tube 24 at a rate of approximately 200 mL/min for approximately 10 minutes.

The sampling canister 20 may also be configured so that a user is able to decontaminate the sampling canister 20 as the sampling canister 20 is removed from the sampled environment. Decontamination may be accomplished without adversely affecting the sample contained within the sampling tube 24. For example, a user may decontaminate the sampling canister 20 by spraying or wiping down the sampling canister 20 with a decontamination agent or by submerging the sampling canister 20 in the decontamination agent. The decontamination agent may be, for example, a quaternary ammonium compound or a hypochlorite solution. Additional decontamination agents include cleaning solvents such as, for example, SIMPLE GREEN®, hypophosphorus acid and sodium nitrate, and potassium nitrate.

The thermal desorption device 30 of the device 10 is configured to promote desorption of the environmental sample captured in the sorbent 23 from the sorbent 23 to yield a gaseous sample for analysis. The thermal desorption device 30 may be any mechanism capable of desorbing the captured sample. In an exemplary embodiment, the thermal desorption device 30 is disposed in the sampling canister 20 and is adapted to increase a temperature of the sorbent 23 to promote desorption of the captured sample. As shown in FIG. 7, the thermal desorption device 30 may include a heating element 32 that is capable of thermal communication with the sorbent 23. For example, the heating element 32 may surround or thermally contact the sampling tube 24. When the heating element 32 is activated, the heating element 32 heats the sorbent 23 to a temperature that is suitable for desorbing the sample from the sorbent 23. The temperature suitable for desorption varies depending on the sorbent material and the particular sample. For example, in one embodiment, desorption of the sample is accomplished by heating the sorbent 23 to a temperature in a range of about 50° C. to about 250° C. In an exemplary embodiment, the sorbent 23 is heated at approximately 20° C. The sorbent may be heated for approximately 30 seconds to approximately 10 minutes.

The thermal desorption device 30 may be used in combination with a temperature sensor 34 that monitors the temperature within the sampling canister 20. As shown in FIG. 7, the temperature sensor 34 may be disposed in the sampling canister 20. The temperature sensor 34 may be any known temperature sensor such as, for example, a thermistor or a thermocouple. In one embodiment, the temperature sensor 34 is an thermal resistive sensor (RTD). Additionally, the device 10 may be configured so that when a desired temperature is reached within the canister 20 in a vicinity of the sampling tube 24, the transfer mechanism 50 is activated. As described below, the transfer mechanism 50 transfers the desorbed gaseous sample from the sampling tube 24 to the gas cell 60 for analysis. In an exemplary embodiment, the desired temperature is within a range of about 130° C. to about 250° C.

Figure 9:
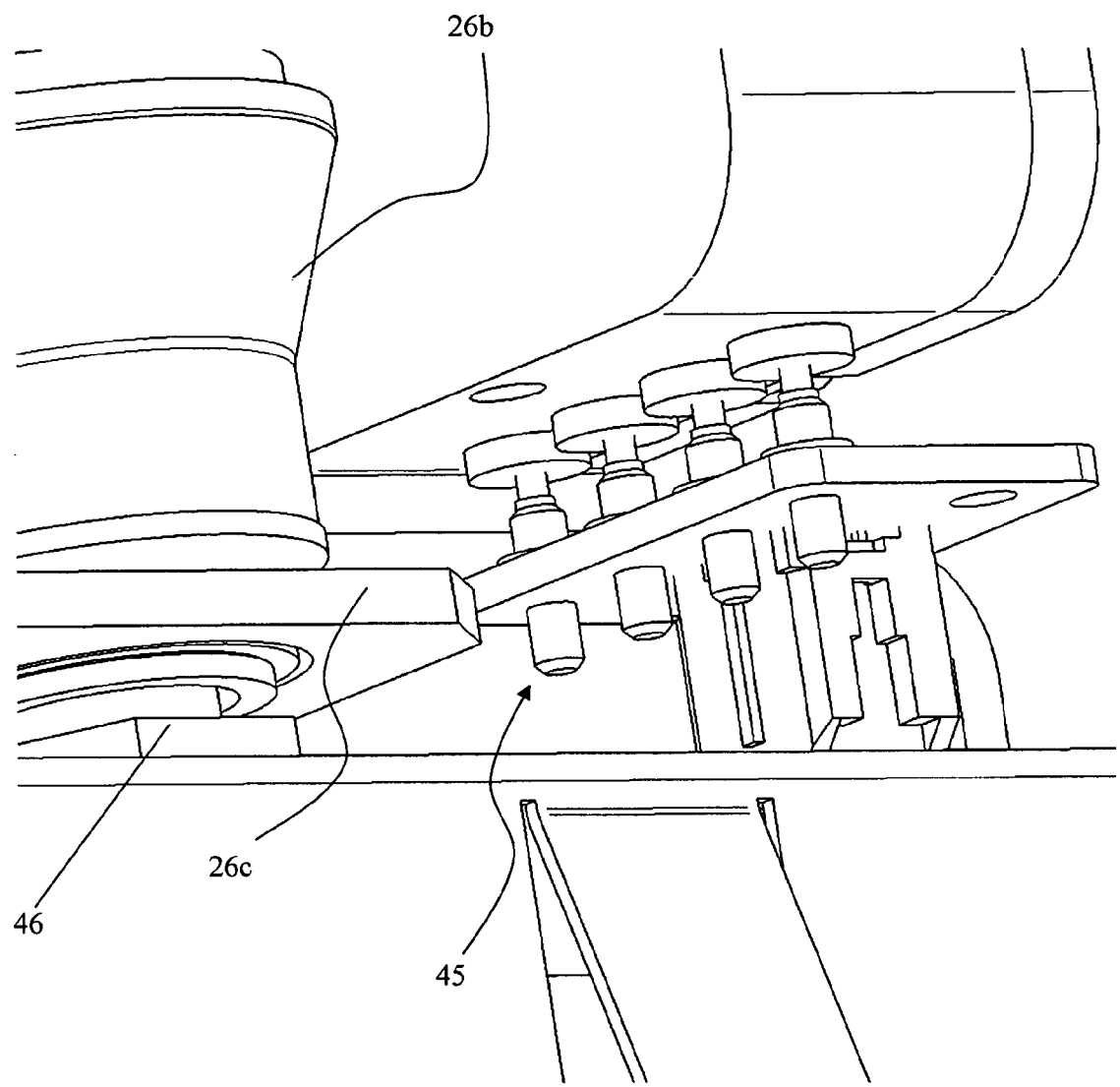
FIG. 9 is a perspective view of electrical contacts of the device of FIG. 1.

As described above, the sampling canister 20 is configured to removably engage or dock with the docking station 40. For example, after the gaseous sample is collected and sealed in the sampling tube 24, the sampling canister 20 may be docked in the docking station 40 for analysis of the gaseous sample. In one embodiment, when the sampling canister 20 is docked with the docking station 40 (shown in FIGS. 1 and 2), the sampling canister 20 is in electrical communication with a power source 110. For example, the docking station 40 may include at least one electrical contact 45 (shown in FIG. 8) that is adapted to be electrically connected with a corresponding electrical contact 25 (shown in FIG. 7) disposed on the sampling canister 20. In an exemplary embodiment, at least one of the electrical contacts 25 and 45 are plunger electrical contacts as shown in FIG. 9. Additionally, as shown in FIG. 9, the sampling canister 20 and the docking station 40 may include multiple electrical contacts 25 and 45, respectively, depending on the power requirements of the sampling canister 20. For example, the sampling canister 20 and the docking station 40 may each include four electrical contacts. When the contacts 25 and 45 are electrically connected (e.g., in contact), electrical power from the power source 110 may be supplied to the canister 20 to power, for example, the heating element 32 and the temperature sensor 34. The power source 110 may be any known power source such as, for example, a battery, a generator, or a standard electrical socket.

Figure 2:
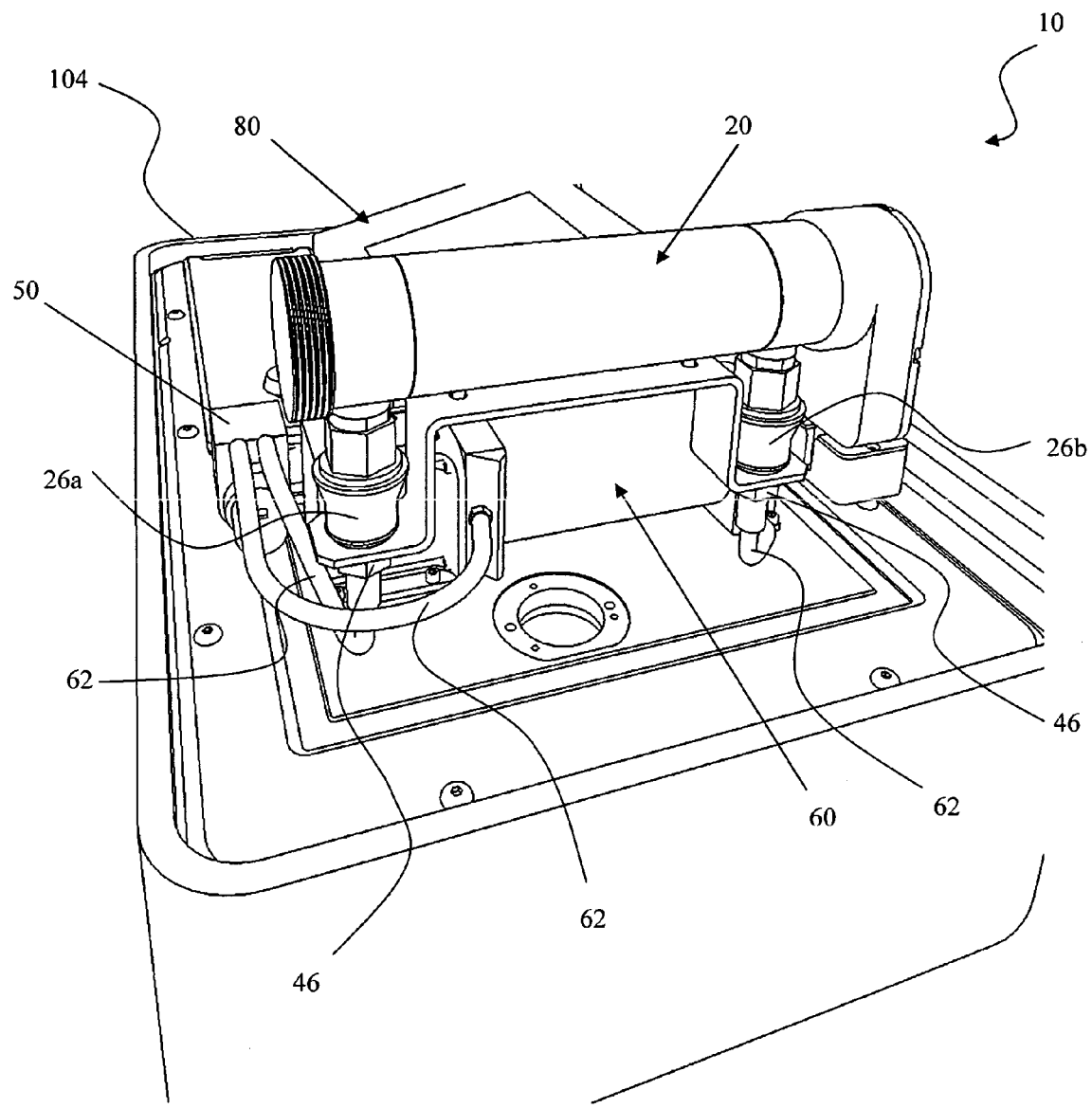
FIG. 2 is a right perspective view of the device of FIG. 1.
Figure 10:
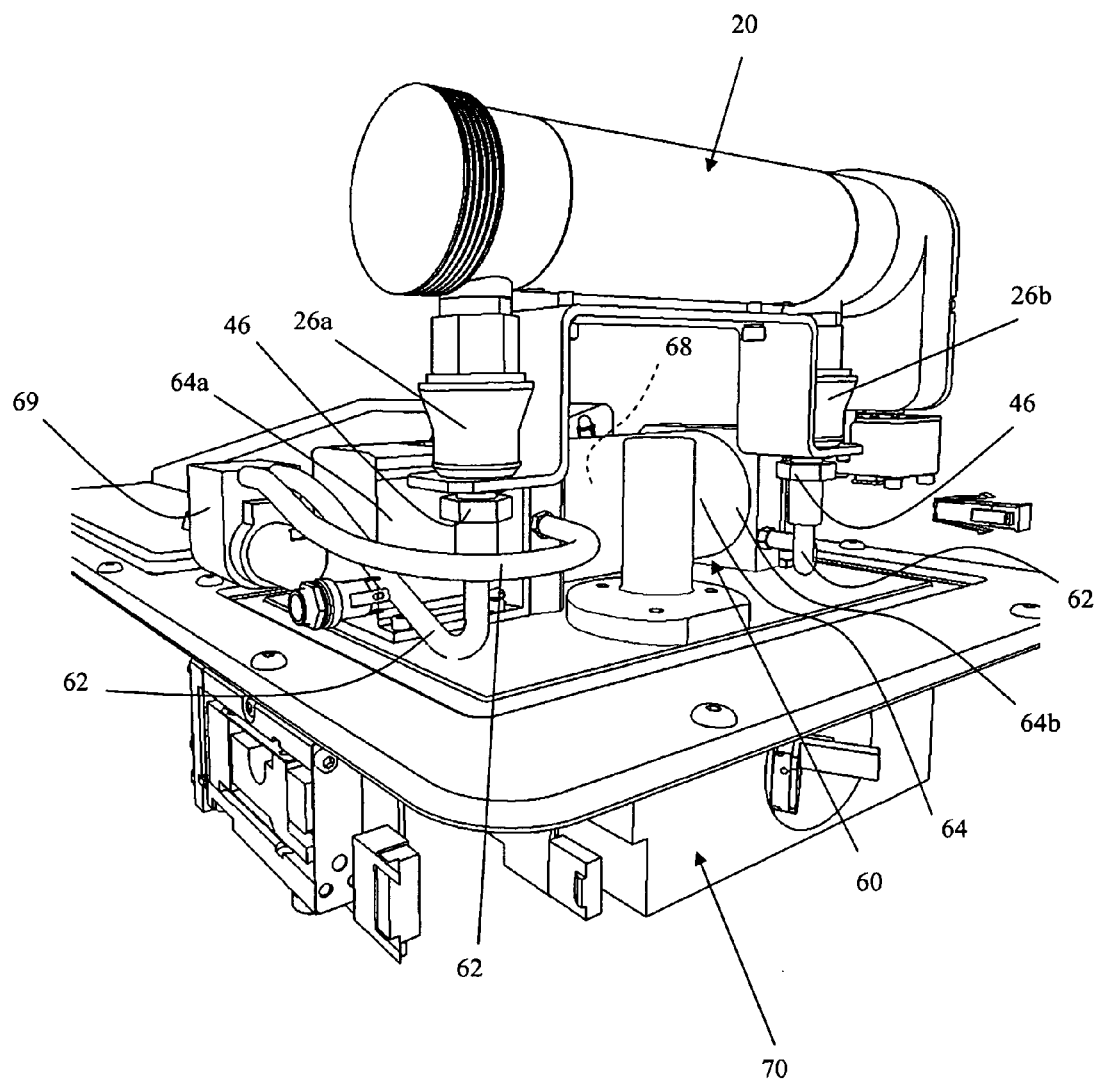
FIG. 10 is a right perspective view of the device of FIG. 1 with a case and covers removed.

The docking station 40 also provides an interface between the sampling canister 20 and the gas cell 60 to enable analysis of the gaseous sample. In an exemplary embodiment, when the sampling canister 20 is docked with the docking station 40, the sampling canister 20 is capable of fluid communication with the gas cell 60. For example, as shown in FIGS. 2 and 10, the gas cell 60 may be connected to the docking station 40 by gas lines 62. The gas lines 62 may include, for example, any known tube, hose, pipe, and/or fitting suitable for use in an airtight system configured to circulate a gaseous fluid. For example, the gas lines 62 may include TEFLON® tubing, silicone tubing, stainless steel tubing, and PEEK™ tubing. In an exemplary embodiment, fluid communication between the gas cell 60 and the sampling canister 20 is accomplished by connecting the valves 26a and 26b of the sampling canister 20 to the corresponding couplings 46 on the docking station 40 substantially as described above so that the valves 26a and 26b are automatically actuated to the open position. When the valves 26a and 26b are open, the sampling tube 24 of the sampling canister 20 is in fluid communication with the gas cell 60 via the gas lines 62. Thus, when the sampling canister 20 is connected to the docking station 40, a closed loop system is established between the sampling canister 20 and the gas cell 60.

The transfer mechanism 50 of the device 10 may be configured to circulate a gas-phase fluid between the sampling canister 20 and the gas cell 60. For example, the transfer mechanism 69 may be a pump, such as an air pump, that is disposed in the closed loop established between the sampling canister 20 and the gas cell 60. As shown in FIG. 2, the transfer mechanism 69 may be connected to the gas lines 62 so that the transfer mechanism 69 comprises a portion of the closed loop system. When the transfer mechanism 69 is activated, a carrier gas contained in the gas cell 60 and the gas lines 62 is circulated through the closed loop system. As the carrier gas circulates through the sampling tube 24, the carrier gas mixes with the desorbed gas sample and carries the desorbed gas sample to the gas cell 60 for analysis. In this manner, the transfer mechanism 69 provides for movement of the desorbed gas sample from the sampling tube 24 to the gas cell 60. In an exemplary embodiment, the carrier gas is the ambient air contained in the gas cell 60 at the start of a sampling experiment. This air is circulated from the gas cell 60 through the transfer mechanism 69 to the sample tube 24 and then back to the gas cell 60, as shown in FIG. 3, thereby forming a closed loop. When the experiment is complete, the sampling canister 20 is removed, and the gas is pumped out of the gas cell 60. A fresh volume of air is drawn into the gas cell 60 to serve as the carrier gas for the next experiment. In one embodiment, the fresh volume of air may be drawn through a filter or desiccant to remove moisture and/or contaminants that may be present in the local atmosphere. The fresh volume from a source of gas other than air such as, for example, a cylinder of nitrogen or other non-infrared active gas.

For example, the carrier gas may be a single gas or a mixture of gases. Any appropriate gas or mixture of gases can be used. In one embodiment, the carrier gas is a gas or mixture of gases that is non-infrared active or is only minimally infrared active so that the carrier gas does not interfere with an infrared measurement performed by the spectrometer 70. For example, the carrier gas may be He, Ne, Ar, $H_2$, $N_2$, and/or $O_2$. In one embodiment, the carrier gas comprises Helium. In an exemplary embodiment, the carrier gas comprises ambient air. The carrier gas may also be air that is substantially free of hydrocarbons such as zero air. The transfer mechanism 69 may be operated at a rate of approximately 1 mL/min to 1000 mL/min. In an exemplary embodiment, the transfer mechanism 69 is operated at a rate of approximately 500 mL/min.

The gas cell 60 is configured to optically manipulate a beam I from the spectrometer 70 to enable analysis of the gaseous sample. The gas cell 60 may be any known gas cell suitable for measuring optical absorption of gas-phase samples. For example, the gas cell 60 may be a folded path cell or a multipath optical cell. As shown in FIG. 10, the gas cell 60 may include a housing 64 with a first end 64*a* and a second end 64*b*. The housing 64 may be made of metal such as, for example, aluminum. The housing 64 houses optical components of the gas cell 60. In an exemplary embodiment, the optical components of the gas cell 60 may include a spherical optic 63 disposed in an objective position and a flat optic 65 disposed in a field position. Additionally, the optics 63 and 65 may define a substantially closed compartment 68 of the gas cell 60. For example, the flat optic 65 may function as an end cap for sealing the first end 64*a* (i.e., the entrance) of the gas cell compartment, and the spherical optic 63 may function as an end cap for sealing the second end 64*b* of the gas cell compartment. The optical components, including windows and mirrors, may be prepared using any suitable materials and may optionally be coated with any suitable coating. The mirrors may be fabricated from, for example, gold-coated aluminum. The window may be made of, for example, $CaF_2$, KBr, $BaF_2$, or ZnSe. In an exemplary embodiment, the flat optic 65 is the window of the gas cell 60 and includes an infrared refracting material that acts as a transmitting window for the beam I. The infrared refracting material may be, for example, $CaF_2$, KBr, $BaF_2$, or ZnSe. Other window materials include Si, Ge, CsI, AgCl, KRS-5, NaCl, and AgBr. In an exemplary embodiment, the flat optic 65 is a ZnSe window coated on both sides with an antireflection coating. In another embodiment, the window may be coated with a thin layer of sapphire for chemical resistance. Moreover, the optical components may be constructed to be resistive to damage from a wide range of chemicals.

Figure 11:
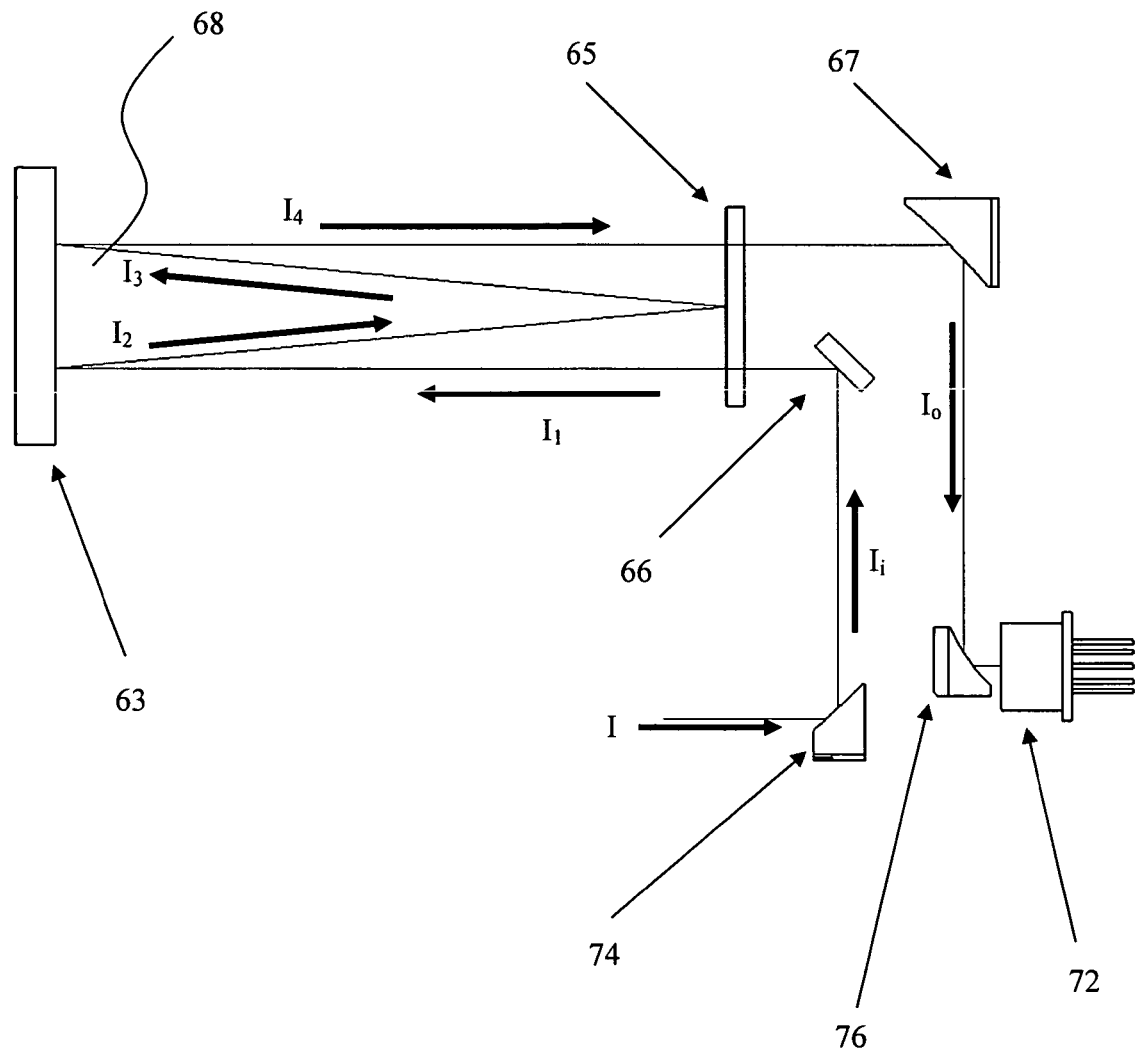
FIG. 11 is a schematic view of an optical configuration of a gas cell of the system of FIG. 1.

The optical components of the gas cell 60 are preferably configured to reduce the physical size of the gas cell 60. For example, the optical components of the gas cell 60 may be configured as a four pass design. To achieve the four pass design, the spherical optic 63 may be adapted to produce two reflections of the beam I in the gas cell compartment 68, and the flat optic 65 may be adapted to produce one reflection of the beam I in the gas cell compartment 68. As shown in FIG. 11, an input component $I_i$ of the beam I from the spectrometer 70 is directed into the gas cell 60 via a flat mirror 66 of the gas cell 60. The beam I makes a first pass $I_1$ through the compartment 68 and is reflected by the spherical optic 63 to make a second pass $I_2$ through the compartment 68. The beam I is then reflected by the flat optic 65 and makes a third pass $I_3$ through the compartment 68. Finally, the beam I is again reflected by the spherical optic 63 to make a fourth pass $I_4$ prior to exiting the compartment 68 through the flat optic 65 as an output beam $I_o$. The output beam $I_o$ is then directed to a detector 72 of the spectrometer 70 by a parabolic mirror 67 of the gas cell 60. In this manner, the optical components of the gas cell 60 provide for four passes ($I_1$, $I_2$, $I_3$, $I_4$) of the beam I through the compartment 68. As a result, the gas cell 60 may be configured to achieve a path length of sufficient length in a gas cell of relatively small volume. For example, the path length may be in a range of approximately 10 cm to 10 m, and the volume may be in a range of approximately 100 $cm^3$ to 1 L In an exemplary embodiment, the path length is approximately 0.422 meters and the gas cell volume is approximately 191 $cm^3$.

The small volume of the gas cell 60 enables the size and mass of the gas cell 60 to be reduced relative to gas cells having comparable path lengths. Thus, the gas cell 60 may be sized so that the gas cell 60 is portable. For example, the gas cell 60 may have a diameter in a range of approximately 25 mm to 100 mm and a length in a range of approximately 50 mm to 1 m. In an exemplary embodiment, a footprint of the gas cell 60 has a diameter of approximately 30 mm, and a length of approximately 100 mm. In another embodiment, a maximum outside width of the gas cell 60 is approximately 3.8 cm (1.5 inches).

The spectrometer 70 of the device 10 is in optical communication with the gas cell 60. As discussed above, the spectrometer 70 produces the beam I and includes a detector 72. The spectrometer 70 may be, for example, a Fourier transform spectrometer. The spectrometer 70 may also be dispersive (grating) or non-dispersive IR (filter). In one embodiment the spectrometer 70 is an infrared spectrometer. The infrared spectrometer can also be a Fourier transform infrared spectrometer. As shown in FIG. 11, the beam I of the spectrometer 70 may be directed into the gas cell 60 by a spectrometer optic 74. After passing through the gas cell 60, the beam I may be directed into the detector 72 of the spectrometer 70 by a detector mirror 76 of the spectrometer 70. In this manner, the spectrometer 70 obtains a spectrum from the gaseous sample. For example, the spectrometer 70 may obtain an infrared spectrum from one or more molecules of the gaseous sample.

The device 10 may also include a computer system 80. The computer system 80 may be configured to monitor and control the operation of the device 10 and/or to analyze data obtained from the spectrometer 70. For example, as a controller, the computer system 80 may be configured to activate the heater 32 after the sampling canister 20 is connected to the docking station 40. The computer system 80 may also be configured to activate the transfer mechanism 50 when the temperature in the vicinity of the sampling tube 24 reaches the desired temperature as indicated by the temperature sensor 34. To facilitate analysis of the gaseous sample, the computer system 80 may include software and hardware for identifying spectra obtained from the gaseous sample. For example, the software in the computer system 80 may be coded to interpret an obtained spectrum of the unknown gaseous sample, such as by comparing the strengths of the various peaks in the spectrum against a database or library of peaks known to correspond to particular functional groups. In one embodiment, the computer system 80 includes a spectral library (database) of known spectra (e.g., infrared spectra) for various functional groups and chemicals. The computers system 80 may provide a list of functional groups or chemicals from the spectral library that correspond to the spectrum of the unknown sample to enable identification of a functional group or chemical contained in the gaseous sample. In an exemplary embodiment, the computer system 80 also provides an indication of the degree of certainty or percentage match of the known spectrum with the unknown spectrum.

As shown in FIG. 1, the computer system 80 may also include a graphical user interface 82 for displaying information. The graphical user interface 82 may display, for example, the unknown spectrum obtained from the gaseous sample, the list of functional groups or chemicals from the spectral library that correspond to the unknown spectrum, a selected spectrum from the spectral library, a chemical name of an identified compound in the gaseous sample, and/or a common name of the identified compound. In addition, the computer system 80 may include user input devices, such as a keyboard or mouse, to allow the user to interact with the computer system 80. Furthermore, the computer system 80 may include hardware and/or software to allow the user to manipulate information provided on the graphical user interface 82.

The device 10 may also include a case 100 within which substantially all of the components previously discussed are disposed. For example, as shown in FIG. 1, the sampling canister 20, the docking station 40, the transfer mechanism 50, the gas cell 60, the spectrometer 70, the computer system 80, and the power supply 110 may be disposed in the case 100. The case 100 may include, for example, a base 102 and a lid 104. The lid 104 can be moved between an open position (shown in FIG. 1) and a closed position (not shown). In the open position, the sampling canister 20, the docking station 40, and the computer system 80 are readily accessible so that a user may operate the device 10. In the closed position, the lid 104 may be latched to the base 102 to secure the case 100 in the closed position. The case 100 may also include a handle to facilitate handling of the case 100 and covers 106 for protecting the various components housed in the case 100.

In an exemplary embodiment, the case 100 is configured to be portable so that the device 10 may be readily transported from one location to another. For example, a width of the case 100 may be in a range of approximately 12 to 32 inches; a depth of the case 100 may be in a range of approximately 8 to 18 inches; and a height of the case 100 (e.g., in the closed position) may be in a range of approximately 6 to 12 inches. In an exemplary embodiment, the width is approximately 17 inches, the depth is approximately 12 inches, and the height is approximately 7.5 inches. Additionally, a weight of the device 10 may be in the range of about 20 to about 50 pounds. In an exemplary embodiment, the weight is about 26 pounds or less. Thus, the device 10 may be configured to have a physical size and weight that enable a user to easily transport the device 10 to various locations.

In operation, the device 10 may be used for collection and analysis of a gaseous sample. According to one embodiment, a method of collecting a gaseous sample from a potentially contaminated environment includes the following steps. The sampling canister 20 is connected to the sampling pump 90, which automatically opens the valves 26a and 26b of the sampling canister 20. The sampling pump 90 is activated and draws a gaseous atmospheric sample from the potentially contaminated environment into the sampling tube 24 of the sampling canister 20. When sampling is complete, the sampling pump 90 is deactivated, and the sampling canister 20 is disconnected from the sampling pump 90, which automatically closes the valves 26a and 26b of the sampling canister 20 and seals the gaseous sample in the sampling tube 24. In the sampling tube 24, the gaseous sample from the environment is adsorbed or absorbed to the sorbent 23 in the sampling tube 24. The sampling canister 20 may also be decontaminated with a decontamination agent as the sampling canister 20 is removed from the potentially contaminated environment.

According to another embodiment, a method of analyzing the gaseous sample collected in the sampling canister 20 includes the following steps. The sampling canister 20 is connected to the docking station 40. When the sampling canister 20 engages the docking station 40, the electrical contacts 25 of the sampling canister 20 contact the electrical contacts 45 of the docking station 40 so that power is supplied to the sampling canister 20. Additionally, upon docking, the valves 26a and 26b of the sampling canister 20 open, which places the sampling tube 24 of the sampling canister 20 in fluid communication with the gas cell 60. The heating element 32 located in the sampling canister 20 is activated. As the sorbent 23 is heated, the gaseous sample from the potentially contaminated environment which was adsorbed or absorbed to the sorbent 23 desorbs from the sorbent 23 back into a gaseous sample. When a temperature in the vicinity of the sampling tube 24 reaches a desired temperature, the transfer mechanism 50 is activated thereby causing at least a portion of the gaseous sample in the sampling tube 24 to flow into the gas cell 60. The gaseous sample may also be mixed with a carrier gas to facilitate transport of the gaseous sample to the gas cell 60. The spectrometer 70 is activated to determine the spectral properties of the components of the gaseous sample in the gas cell 60. An obtained spectrum of the gaseous sample is compared with a set of known spectra stored in the computer system 80. To facilitate identification of the obtained spectrum, the computer system 80 may be utilized to compare the obtained unknown spectrum with a database of known spectra to determine the chemical composition of the unknown spectrum obtained from the gaseous sample.

Thus, the above-described embodiments provide a system and method for the collection and identification of unknown chemicals in a gaseous sample from a potentially contaminated environment. The system may be configured to be durable and portable. As a result, the system is suitable for use by HAZMAT teams, facility security professionals, military forces, and first responders to identify potential chemical hazards at locations on-site and in the field.

The following example is given to illustrate the present invention. It should be understood, however, that the invention is not to be limited to the specific conditions or details described in these examples.

EXAMPLE

This example demonstrates the application of thermal desorption (TD) in combination with FTIR for identification of a variety of toxic and hazardous substances at an identification limit (IL) of one half its IDLH value (Immediately Dangerous to Life and Health, an OSHA standard). The IL ranges from <1 ppm to thousands of ppm, depending on the compound. IL is defined as the concentration of a compound that produces a sufficiently high signal-to-noise spectrum to result in a spectral library match of that compound with a dot product correlation of 0.90 (scale of 0 to 1).

The detection of methane, propane, n-pentane, acetone, isopropanol, toluene, m-xylene, 1,2-dichlorobenzene, n-dodecane, nicotine, 1-dodecanol, ethanol, methanol, ammonia, and thiodiethanol is tested. Several sorbents, including TENAX® TA, TENAX® GR, and carbon molecular sieve based materials, are tested to determine which sorbent is most effective.

Each analyte is tested individually to determine the best sorbent for the widest range of analytes. First, a known test environment is established by injecting a known volume of a known gases or volatile liquid into a 140 L chamber having a sampling port. To establish the validity of this approach, the equilibrium concentration is determined to ensure that the known equilibrium concentration is established within the chamber using this technique. Second, the environment is sampled by drawing a gas sample from the chamber via ¼ in. tubing through a 8×110 mm tube containing 150 mg total sorbent using a battery-operated hand pump (SKC, Inc) at 200 mL/min for 10 min. Third, the analytes are desorbed by encapsulating the sampling chamber containing sorbent within a holder that connects directly to the FT-IR gas cell in a closed-loop arrangement. The tube is heated to 200° C. to desorb the analyte from the sorbent. Finally, a desorption pump rate operating at approximately 500 mL/min circulated desorbed analyte to the gas cell for examination by FTIR spectroscopy.

Initial experiments indicate that TENAX® TA is a useful sorbent for the variety of analytes tested. Table 1 shows data obtained using methane, propane, n-pentane, acetone, isopropanol, touene, m-xylene, 1,2-dichlorobenzene, n-dodecane, nicotine, and 1-dodecanol. The table provides the boiling points and corresponding breakthrough volumes (BVs) using TENAX® TA. Analytes are listed in ascending order of boiling point. The concentration factors are calculated as (ppm in FT-IR cell)/(ppm in chamber), and the "best sorbent" is that which produced the highest concentration factor. Analyte concentrations in the FT-IR gas cell are determined by least-squares fitting with quantitative infrared spectral data from Pacific Northwest National Labs (PNNL). The data shows that low boiling analytes are more difficult to trap, while high boiling analytes are more difficult to get into the vapor phase for analysis.

one versed in the art from the present disclosure within the scope and spirit of the present invention are to be included as further embodiments of the present invention. The scope of the present invention is to be defined as set forth in the following claims.

What is claimed is:

1. A system for identifying a gas sample, the system comprising:
    a canister including a sorbent and a valve;
    a docking station for removably engaging the canister, wherein the canister is capable of fluid communication with a gas cell via the valve when the canister is engaged with the docking station;
    a thermal desorption device disposed within the canister; and
    a spectrometer,
wherein the system is capable of identifying a compound in the gas sample.

2. The system of claim 1, wherein the canister, the docking station, the thermal desorption device, the gas cell, and the spectrometer are disposed in an enclosure.

3. The system of claim 2, wherein the enclosure comprises a portable case.

4. The system of claim 1, wherein the valve includes a first valve and a second valve.

5. The system of claim 1, wherein the valve includes two valves in communication with a control mechanism for actuating the valves.

6. The system of claim 1, wherein the valve is configured to automatically open when a pump is connected to the valve and to automatically close when the pump is disconnected from the valve.

7. The system of claim 1, wherein the valve opens automatically when the canister engages the docking station.

TABLE 1

Thermal Desorption Data

| Compound | bp (° C.) | BV (L/ 150 mg TENAX ® @ 20 C.) | Lowest ppm tested | Resulting ppm calc | Conc. Factor | Best sorbent |
|---|---|---|---|---|---|---|
| Methane | −162 | 0.0009 | 61 | n/a | n/a | n/a |
| Propane | −42 | 0.022 | n/a | 185 | n/a | Anasorb 747 |
| n-Pentane | 36 | 0.75 | 100 | 175 | 1.75 | TENAX ® TA |
| Acetone | 56 | 0.9 | 50 | 100 | 2 | TENAX ® TA |
| Isopropanol | 82 | 0.75 | 100 | 180 | 1.8 | TENAX ® TA |
| Toluene | 111 | 60 | 100 | 272 | 2.72 | TENAX ® TA |
| m-Xylene | 139 | 233 | 100 | 319 | 3.19 | TENAX ® TA |
| 1,2-Dichlorobenzene | 181 | 495 | 50 | 121 | 2.42 | TENAX ® TA |
| n-Dodecane | 216 | 7500 | 50 | 57 | 1.14 | TENAX ® TA |
| Nicotine | 245 | 15000 | 100 | 26 | 0.26 | TENAX ® TA |
| 1-Dodecanol | 256 | 210000 | 100 | n/a | n/a | TENAX ® TA |

Given the disclosure of the present invention, one versed in the art would appreciate that there may be additional embodiments and modifications within the scope and spirit of the invention. Accordingly, all modifications attainable by 8. The system of claim 1, wherein the sorbent is contained in a tube disposed in the canister.

9. The system of claim 8, wherein the tube comprises glass.

10. The system of claim 8, wherein the tube is a disposable tube configured to be discarded after the gas sample is collected and analyzed.

11. The system of claim 1, wherein the thermal desorption device includes a heating element and an electrical contact adapted to be electrically connected with a corresponding electrical contact disposed on the docking station.

12. The system of claim 11, further comprising a temperature sensor disposed in the canister and a transfer mechanism configured to be activated when a temperature in the canister reaches a desired temperature.

13. The system of claim 12, wherein the desired temperature is within a range of about 130° C. to about 250° C.

14. The system of claim 11, wherein at least one of the electrical contact of the docking station and the electrical contact of the thermal desorption device comprises a plunger electrical contact.

15. The system of claim 1, further comprising a transfer mechanism for transferring a fluid disposed in the canister to the gas cell.

16. The system of claim 15, wherein the transfer mechanism comprises a pump.

17. The system of claim 1, further comprising a computer system in communication with the spectrometer and including a spectral library stored within the computer.

18. The system of claim 17, wherein the computer system includes a graphical user interface for displaying a infrared spectrum from the gas sample, a selected infrared spectrum from the spectral library, a chemical name of an identified compound from the gas sample, and/or a common name of the identified compound.

19. The system of claim 1, wherein the gas cell has a path length in a range of about 10 cm to about 10 m and a volume in a range of about 100 $cm^3$ to about 1 L.

20. The system of claim 19, wherein the path length is approximately 0.4 meters and the volume is approximately 190 cubic centimeters.

21. The system of claim 1, wherein the gas cell comprises a compartment that includes a flat portion for folding a beam of the spectrometer and for entrance and exit of the beam from the gas cell and further comprises a spherical portion, wherein the beam of the spectrometer passes through the compartment four times.

22. The system of claim 21, wherein the flat portion comprises an end cap of the gas cell.

23. The system of claim 21, wherein the flat portion includes an infrared refracting material capable of transmitting an infrared beam.

24. The system of claim 23, wherein the infrared refracting material is selected from the group consisting of $CaF_2$, KBr, $BaF_2$, ZnSe, Si, Ge, CsI, AgCl, KRS-5, NaCl, and AgBr.

25. The system of claim 23, wherein the infrared refracting material includes ZnSe.

26. The system of claim 1, wherein the spectrometer comprises a Fourier transform infrared spectrometer.

27. The system of claim 1, wherein the spectrometer comprises an infrared spectrometer.

28. The system of claim 1, further comprising a gas cell, wherein the gas cell comprises:
a housing defining a substantially closed compartment;
a spherical optic in an objective position; and
a flat optic in a field position,
wherein the flat optic is configured to permit a beam to enter and exit the compartment, and
wherein the spherical optic is configured to produce two reflections of the beam in the compartment and the flat optic is configured to produce one reflection of the beam in the compartment so that the beam passes through the compartment four times.

29. A method for identifying a gaseous sample, comprising:
providing a sorbent disposed in a tube;
adsorbing an atmospheric gas to the sorbent;
desorbing the atmospheric gas from the sorbent to yield a gaseous sample;
circulating a carrier gas through the tube so that the carrier gas mixes with the gaseous sample;
transferring the gaseous sample to a gas cell;
activating a spectrometer in optical contact with the gas cell;
obtaining a spectrum of the gaseous sample;
comparing the obtained spectrum of the gaseous sample with a set of known spectrum values;
identifying a compound in the gaseous sample; and
recirculating the gaseous sample or readsorbing the gaseous sample to the sorbent.

30. The method of claim 29, wherein the carrier gas is air.

31. The method of claim 29, further comprising the step of opening a valve to allow the atmospheric gas and/or the carrier gas to enter the tube.

32. The method of claim 31, further comprising the step of connecting a pump to the valve.

33. The method of claim 31, further comprising the step of engaging the valve with a docking station.

34. The method of claim 33, further comprising electrically connecting the tube and the docking station via an electrical contact on the docking station and a corresponding electrical contact on the tube.

35. The method of claim 29, further comprising the step of heating the tube.

36. The method of claim 35, further comprising the step of activating a transfer mechanism to transfer the gaseous sample from the tube to the gas cell when a desired temperature is reached in a vicinity of the tube.

37. The method of claim 36, wherein the desired temperature is in a range of about 130° C. to about 250° C.

38. The method of claim 29, wherein the step of transferring the gaseous sample comprises activating a pump.

39. The method of claim 29, wherein the step of recirculating the gaseous sample or readsorbing the gaseous sample to the sorbent consists essentially of recirculating the gaseous sample to the sorbent.

40. The method of claim 29, wherein the step of recirculating the gaseous sample or readsorbing the gaseous sample to the sorbent consists essentially of readsorbing the gaseous sample to the sorbent.

41. The method of claim 29, further comprising the step of providing a computer system in communication with the spectrometer.

42. The method of claim 41, further comprising the step of providing the computer system with a spectral library containing known infrared spectrum values.

43. The method of claim 41, further comprising the step of displaying on a graphical user interface of the computer system an infrared spectrum from the gaseous sample, a selected infrared spectrum from the spectral library, a chemical name of an identified compound of the gaseous sample, and/or a common name of the identified compound.

44. The method of claim 29, further comprising the step of passing an infrared beam from the spectrometer through the gaseous sample at least four times.

45. The method of claim 29, wherein the spectrometer is an infrared spectrometer and the obtained spectrum is an infrared spectrum.

46. The method of claim 45, wherein the spectrometer is a Fourier transform infrared spectrometer.

47. The method of claim 29, further comprising the step of returning a list of gases having spectra substantially similar to the obtained spectrum of the gaseous sample.

48. A portable device for analyzing a gaseous sample, comprising:
   a canister, wherein a sorbent is disposed within the canister;
   a thermal desorption device disposed within the canister;
   a gas cell in optical communication with a spectrometer;
   a docking station configured for removable engagement with the canister, wherein the canister is adapted for fluid communication with the gas cell when the canister is engaged with the docking station; and
   a computer system for analyzing data from the spectrometer, wherein the computer system is capable of identifying a compound in the gaseous sample.

49. The portable device of claim 48, wherein the spectrometer comprises an infrared spectrometer.

50. The portable device of claim 48, wherein the spectrometer comprises a Fourier transform infrared spectrometer.

51. The portable device of claim 48, wherein the computer system includes software, hardware, or software and hardware for comparing a spectrum obtained from the gaseous sample by the spectrometer to known spectra included in a spectral library stored in the computer system.

52. The portable device of claim 48, wherein the canister, the gas cell, the spectrometer, the docking station, and the computer system are housed in a portable case.

53. The portable device of claim 48, further comprising a battery.

* * * * *